Figure 1:
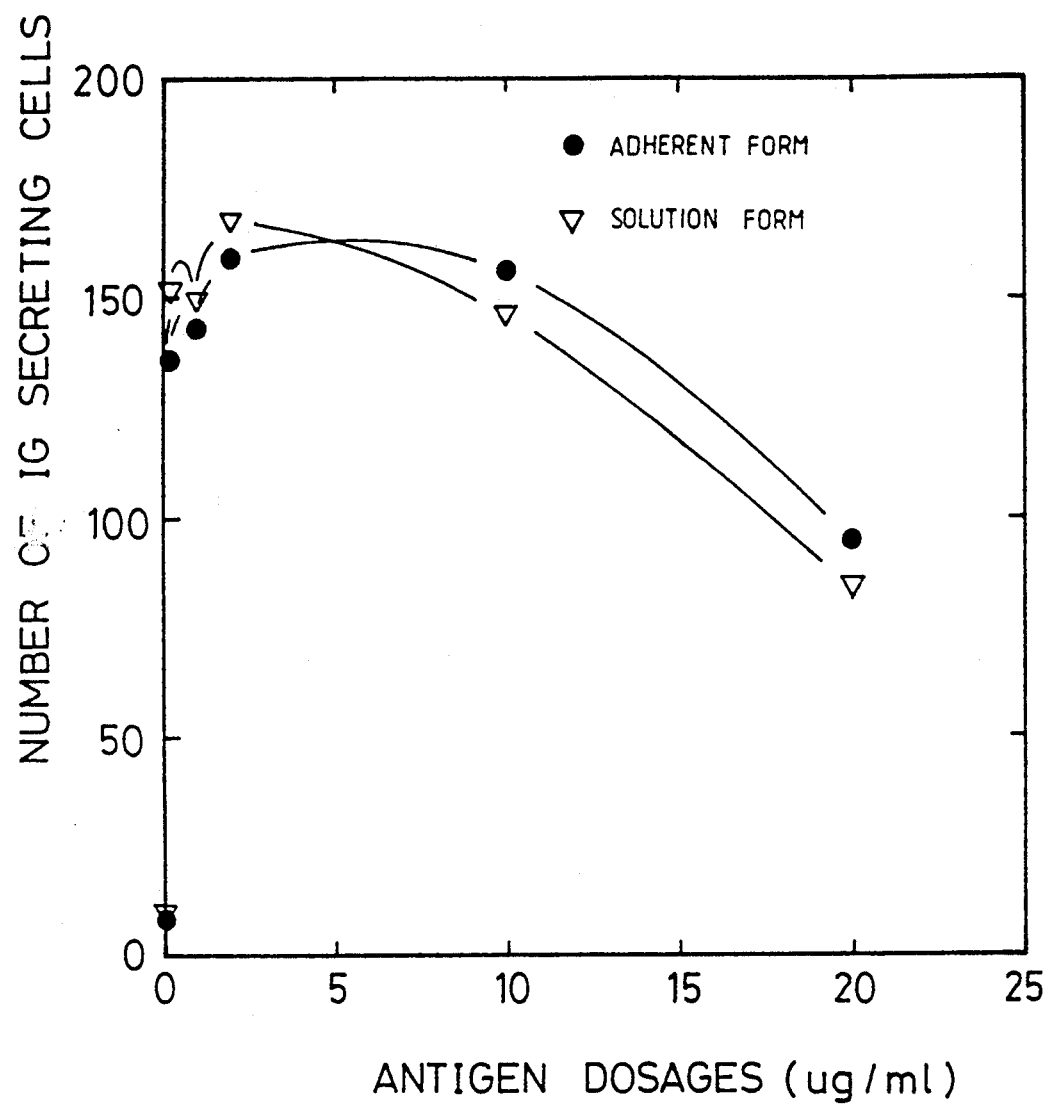

United States Patent [19]

Liu et al.

[11] Patent Number: 5,283,066
[45] Date of Patent: Feb. 1, 1994

[54] METHOD OF STIMULATING AN IMMUNE RESPONSE BY USING A HAPTEN

[75] Inventors: Jiuan J. Liu; Chun-Chieh Wang; Yuang-Ling Hwang; Tong H. Chang, all of Taipei, Taiwan

[73] Assignee: Development Center for Biotechnology, Taipei, Taiwan

[21] Appl. No.: 837,747

[22] Filed: Feb. 19, 1992

[51] Int. Cl.$^5$ .................... A61K 9/14; G01N 33/544; G01N 33/545

[52] U.S. Cl. .................................... 424/484; 514/885; 424/489; 436/535; 436/570; 436/531; 436/534

[58] Field of Search ................ 549/469, 470; 424/484, 424/78.08, 485, 486, 488, 484, 78.08; 436/530, 518, 534, 523, 524, 529, 531, 543, 535; 514/822

[56] References Cited

U.S. PATENT DOCUMENTS

| | | | |
|---|---|---|---|
| 3,547,955 | 12/1970 | Scharpf | 549/470 |
| 4,689,220 | 8/1987 | Sturmer et al. | 424/85 |
| 4,788,217 | 11/1988 | Lanyi et al. | 549/470 |
| 4,834,973 | 5/1989 | Strahilevitz | 424/85.8 |
| 4,863,735 | 9/1989 | Kohn et al. | 424/89 |
| 4,879,225 | 11/1989 | Morgan, Jr. et al. | 435/68 |
| 4,957,737 | 9/1990 | Heimer et al. | 424/88 |
| 5,075,109 | 12/1991 | Tice et al. | 424/439 |
| 5,087,638 | 2/1992 | Belanger et al. | 549/469 |

OTHER PUBLICATIONS

Dinjens et al., "Solid-phase adsorption of antigens for efficient production of antibodies reactive with native and fixed tissue antigens", Journal of Immunological Methods 126:175-182, 1990.

Shields et al., "An appraisal of polystyrene-(ELISA) and nitrocellulose-based (ELIFA) enzyme immunoassay systems using monoclonal antibodies reactive toward antigenically distinct forms of human C-reactive protein", Journal of Immunological Methods 141:253-261, 1991.

Primary Examiner—Thurman K. Page
Assistant Examiner—Peter F. Kulkosky
Attorney, Agent, or Firm—Fish & Richardson

[57] ABSTRACT

Disclosed is a method of stimulating an immune response by using a hapten. Haptens are adhered onto a solid phase support to form a complex. This complex can stimulate an immune response of an animal and the animal's lymphocytes. The solid phase supports usable in the method preferably are membranes, latex particles or microparticle beads of hydrophilic cellulose mixed ester, nitrocellulose, cellulose acetate, nylon, polyvinylidone, vinylbenzyl chloromethyl styrene, polyacrolein, a ahydrophobic, polytetrafluoroethylene, polystyrene and silica gel.

20 Claims, 4 Drawing Sheets

METHOD OF STIMULATING AN IMMUNE RESPONSE BY USING A HAPTEN

BACKGROUND OF THE INVENTION

The present invention relates to a method of stimulating an immune response by using a hapten, in particular to a method of stimulating an immune response by using a hapten dried onto a solid support.

A hapten is a substance which can bind with an antibody, but is not capable of stimulating an immune response when presented alone. Most of the haptens are small molecular substances such as, e.g., drugs, hormones, small peptides and the like, that have a molecular weight lower than 1,000. However, if hapten is linked to a large molecule (which is used as a carrier) the hapten might then appear immunogenic. In order to stimulate an immune response by using a hapten, a conventional method comprises forming an analogue of the hapten, which contains a linking group (spacer arm) having a reactive group, for example, a carboxylic group, at its terminal end; binding the analogue to a carrier, usually a large molecule, for example a protein like BSA, by the reaction of the reactive group with, for example, the amino acid residues of the protein, to form a conjugate, and then stimulating an immune response of an animal and the animal's lymphocytes with this conjugate (Method Enzyme 70,85, 1980). This conventional method is complicated in that chemical synthesis steps are required. Furthermore, whether a hapten-specific immune response can be stimulated is dependent on various factors, such as, e.g., the length and the structure of the linking group, the binding site, the conjugation method, the physiochemical characteristics of the conjugate, the stability of the conjugate, and the ratio between the hapten and the carrier (J. Imm. Method 78:59, 1985; Imm. Methods, Acad. Press 137, 1979; J. Imm. Method 129:119, 1990; Method Enzyme 70:85, 1980; Immunoassays for Trace Chemical Analysis, Chapter 2, 1991). In addition, the immune response will not only react with the hapten, but also react with the linking group and the carrier, and therefore add to the difficulty in screening.

SUMMARY OF THE INVENTION

It is therefore an object of the present invention to provide a novel method of stimulating an immune response by using a hapten, which simplifies the procedure, saves the time and the screening steps.

This object can be attained by providing a method, which comprises preparing a solution of a hapten; adhering the hapten solution to an solid phase support; drying the solid phase support, and stimulating an immune response of an animal and animal's lymphocytes using the hapten-solid support complex.

BRIEF DESCRIPTION OF THE DRAWINGS

The object, features, and advantages of the present invention can be better understood from the following detailed description, examples and accompanied drawings, in which;

FIG. 1 is a graph showing the immunization effect in vitro of a carbofuran-BSA conjugate either adhered onto a nitrocellulose membrane (an adherent form) or in a solution form;

FIG. 2 is a graph showing the immunization effect in vitro of carbofuran monomers either adhered onto a nitrocellulose membrane (an adherent form) or in a solution form;

FIG. 3 is a graph showing the immunization effect in vitro of methamidophos monomers adhered onto a nitrocellulose membrane; and FIG. 4 is a graph showing the immunization effect in vivo of carbofuran monomers adhered onto a nitrocellulose membrane.

DESCRIPTION OF THE INVENTION

The haptens used in this invention are those that can stimulate an immune response by a conventional immunization method using hapten-carrier conjugate, for example water soluble and insoluble chemical substances, drugs, small polypeptides, lipo-polysaccharides and nucleic acids.

The solid phase support usable in this invention are those that have the capability of adhering the above haptens, for example, hydrophilic cellulose mixed ester, nitrocellulose, nylon, polyvinylidone (PVDF), vinylbenzyl chloromethyl styrene, polyacrolein, and hydrophobic polytetrafluoroethylene, polystyrene, silica gel and the like. These materials are used in the form of a membrane, latex particles or microparticle beads. Nitrocellulose membranes, polyvinylidone (PVDF) membranes, nylon membranes, due to an affinity to the hydrophilic or hydrophobic proteins, are particularly preferred. These membranes are also used in Western Blotting or Dot-ELISA.

The present invention will be more clearly understood from the following examples and the comparative example.

COMPARATIVE EXAMPLE 1

An in Vitro Immunization Method of a Carbofuran, a Hapten Pesticide

This comparative example illustrates a conventional method of stimulating an immune response by using a hapten-carrier conjugate.

Carbofuran, which is used as a hapten in this comparative example, is a pesticide of carbamate, which is hardly soluble in water (30° C., a solubility of 700 mg/l water), and has a small molecular weight (MW=221) represented by a structural formula of:

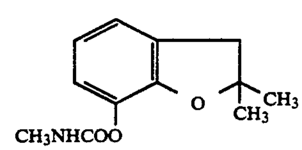

1. Synthesis of an analogue of a hapten (carbofuran)

An analogue of a carbofuran was synthesized by the following reaction scheme:

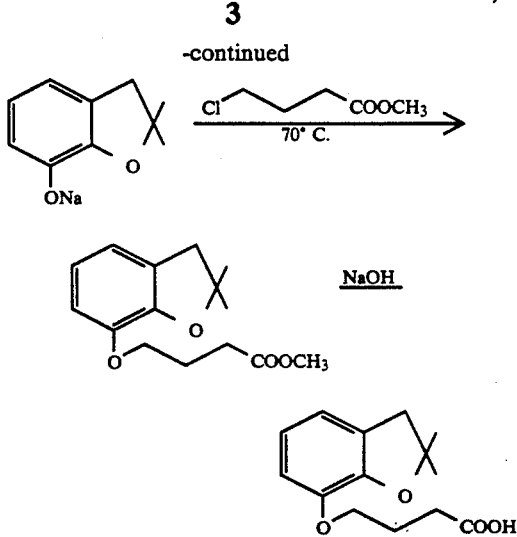

2. Preparation of carbofuran-BSA conjugate

The carbofuran analogue was conjugated to a carrier BSA according to mixed anhydride method (referred to J. Pharm. Sci. 69: 1419-1423, 1980) in a molar ratio (carbofuran/BSA) of 41.

3. Immunization in vitro of BALB/c mice spleen cells with a carbofuran-BSA conjugate Spleen cells were obtained from normal BALB/c mice of 6 to 10 weeks old and the cells were counted. Then, the cells were diluted to a concentration of $2 \times 10^6$/ml and suspended in a serum-free L DM (J. Imm. Meth. 121: 253-260, 1989). To each well of a 6-well tissue culture plate, 1.5 ml of mice's spleen cells, 1.6 ml of thymus conditioned medium (J. Imm. Method 121: 253-260, 1989), 0.1 ml each of concanavalin A (5 μg/ml) and LPS (5 μg/ml) were added in that order. Following that, the carbofuran-BSA was formulated into a final concentration of 0.02 to 20 μg BSA/ml and added into the culture prepared directly in a volume of 0.1 ml (a solution form). The carbofuran-BSA solution was also added onto a sterilized, nitrocellulose membrane having a size of $2 \times 2$ cm$^2$ in an amount of 0.1 ml (an adherent form). The nitrocellulose membrane was then air-dried and been placed on the bottoms of the wells containing cells and medium.

EXAMPLE 1

This example illustrates the method of stimulating an immune response in vitro according to the invention by using a hapten (carbofuran).

0.1 ml of carbofuran monomer (dissolved in methanol and diluted with PBS to a concentration of 0.02-20 μg/ml) was added onto each sterilized nitrocellulose membrane of $2 \times 2$ cm$^2$ (an adherent form), and then followed by air-drying. The nitrocellulose membranes adhered with hapten were placed on the bottom of the wells containing the medium and cells as described in the Comparative Example 1. At the same time, carbofuran solution (a solution form) was added in the same amount to the well. Furthermore, a hapten-free nitrocellulose membrane in the same size and a carbofuran free culture medium in the same amount were used as controls. The cells were cultured in an incubator at 37° C. (containing 5% $CO_2$ and 95% of air). 500 viable cells thus immunized in vitro were sampled on the 5th day and the numbers of the antibodies secreting immune B cells against carbofuran were determined by a Filter-Immune Plaque Assay (J. Imm. Method 179: 195-204, 1985). The assay comprises adhering the hapten, 10 μg carbofuran monomers, 0.1 ml, onto a nitrocellulose membrane first, then blocking with 0.1% of skim milk after drying, and then, placing 500 immunized cells in. Following culturing for 3 hours at 37° C., cells were washed away, and then the antibodies secreted in-situ were color developed with addition of biotin-rabbit anti-mouse Ig (H+L), followed by streptoavidin-horseradish peroxidase (HRPO) and a chromogenic substrate 4-chloro-1-naphthol. The numbers of the antibody-secreting cells (plaque) were counted under a microscope.

Figure 2:
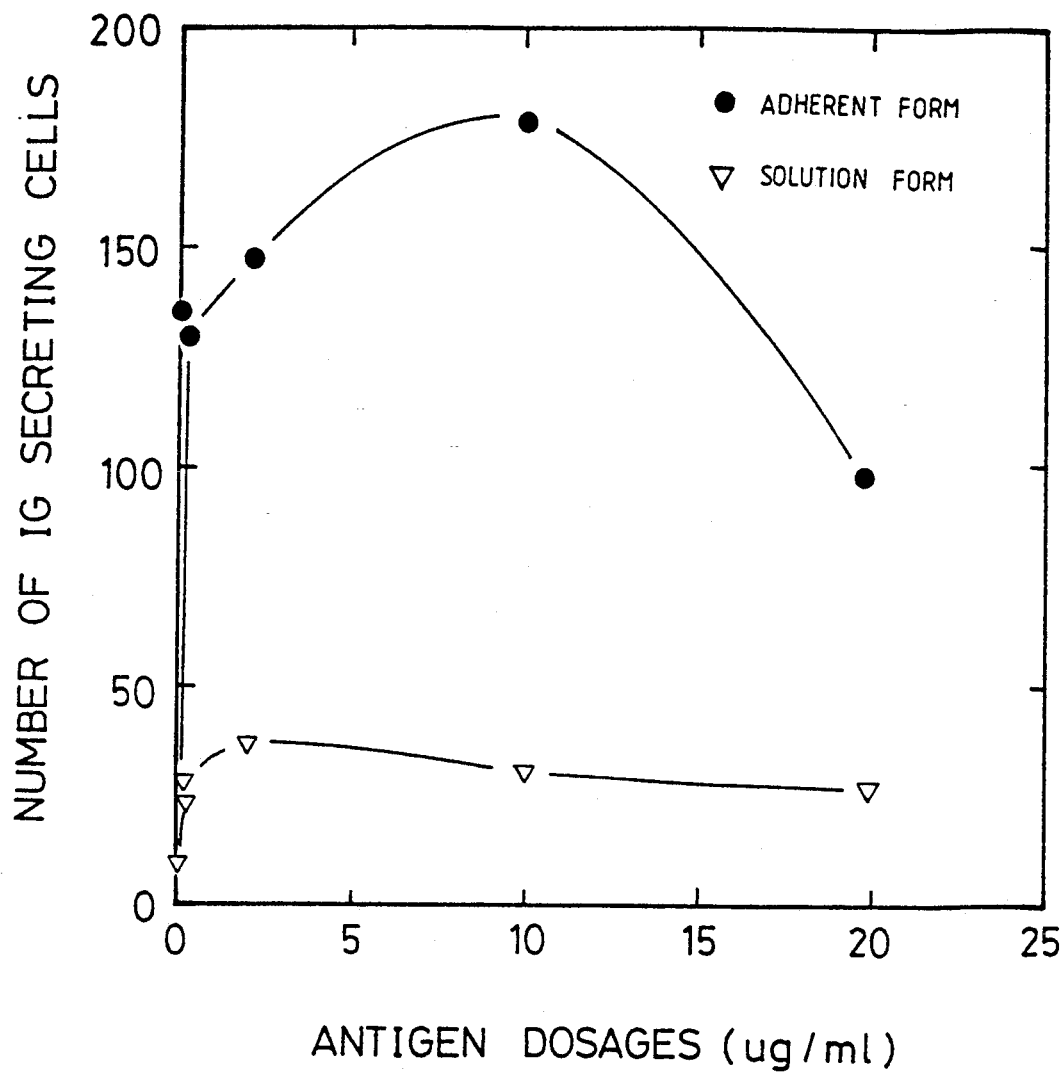

Results of the above Comparative Example 1 and Example 1 are showed in FIGS. 1 and 2.

FIG. 1 shows that whether the carbofuran-BSA was in a solution form or in an adherent form (adhering onto a nitrocellulose membrane), following five days of immunization in vitro, a comparable numbers of immune cells capable of secreting antibodies against carbofuran were produced. Also the numbers of plaques were in a dose-dependent relationship in accordance with the amount of the antigen added. The antigen-free group hardly had any reaction. As shown in FIG. 2, when carbofuran monomer was used as an antigen, only while adhered onto a nitrocellulose membrane (an adherent form) efficiently produced cells capable of secreting antibodies against carbofuran. Accordingly, it is obvious that the method of the present invention can effectively stimulate an immune response in vitro against the hapten, carbofuran in BALB/c mice's spleen cells.

EXAMPLE 2

Figure 3:
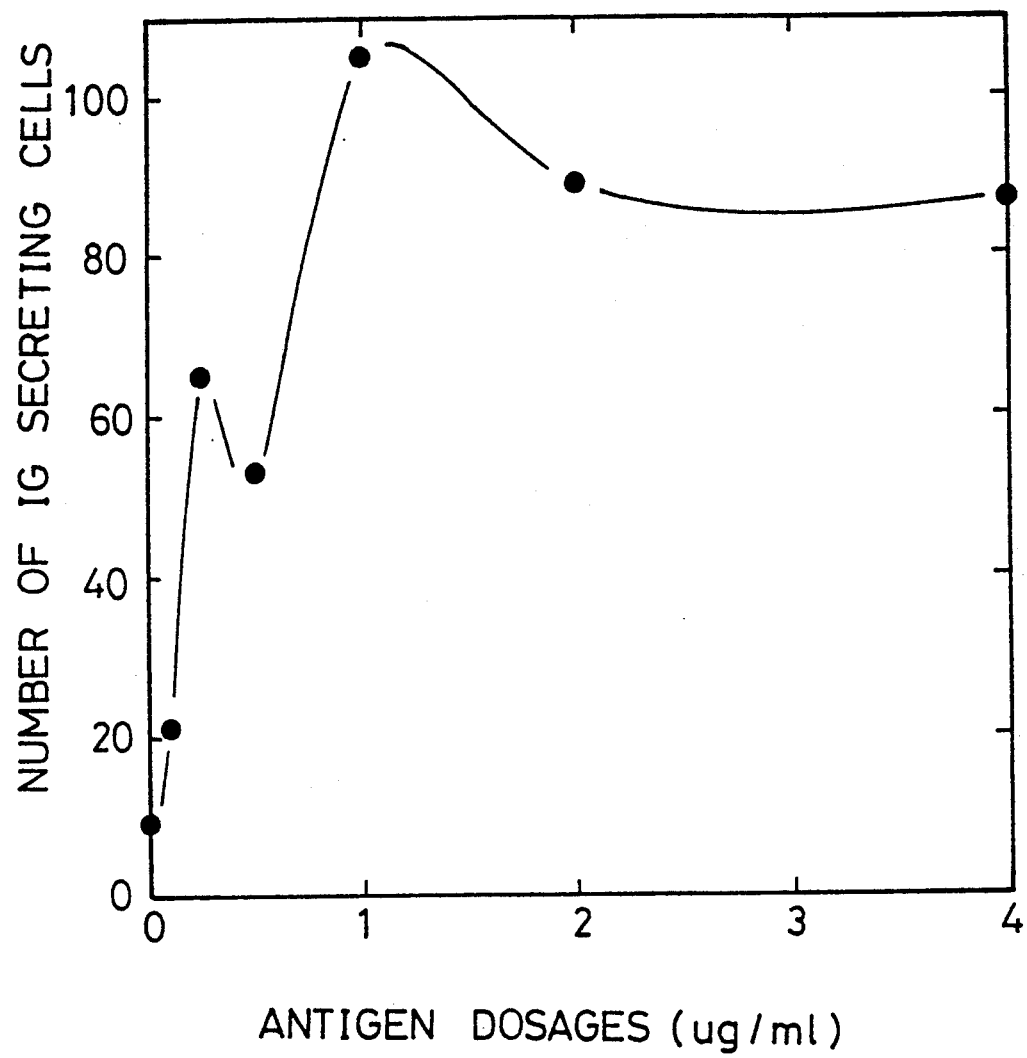

Immunization in Vitro of BALB/c Mice Spleen Cells with a Hapten Pesticide, Methamidophos Methamidophos is a water soluble pesticide of an organic phosphorus group, having a molecular weight of 146. Methamidophos was dissolved in a PBS directly, by the same method as described in Example 1. After that, the concentration was diluted to 0.1-4.0 μg/ml and the solution was absorbed onto sterilized nitrocellulose membranes of $2 \times 2$ cm$^2$. Following air-drying, these membranes were placed respectively in 6 wells, containing cells and conditioned culture medium and then, after being cultured for 4 days in a 37° C. incubator (containing 5% of $CO^2$ and 95% of air), cells were taken and the numbers of cells capable of secreting antibody against methamidophos were determined by means of Filter Immune Plaque Assay. The results are as shown in FIG. 3. As shown in FIG. 3, the number of antibody-secreting cells was in a dose-dependent relation with the dose of the antigen. This indicates that if a water-soluble hapten of a small molecule is adhered onto a nitrocellulose membrane, it can effectively stimulate an immune response in vitro.

EXAMPLE 3

Immunization in Vivo Using a Hapten Pesticide Carbofuran, Adhered onto Nitrocellulose Membrane Carbofuran was dissolved in methanol and then adhered onto nitrocellulose membrane of 1 cm$^2$ in a dose of 20 μg in 0.1 ml of PBS). Following air-drying, the membrane was cut into 4 pieces and implanted subcutaneously to both sides of the neck and the inguinal region of each of 5 normal BALB/c mice of 6-10 weeks old.

Figure 4:
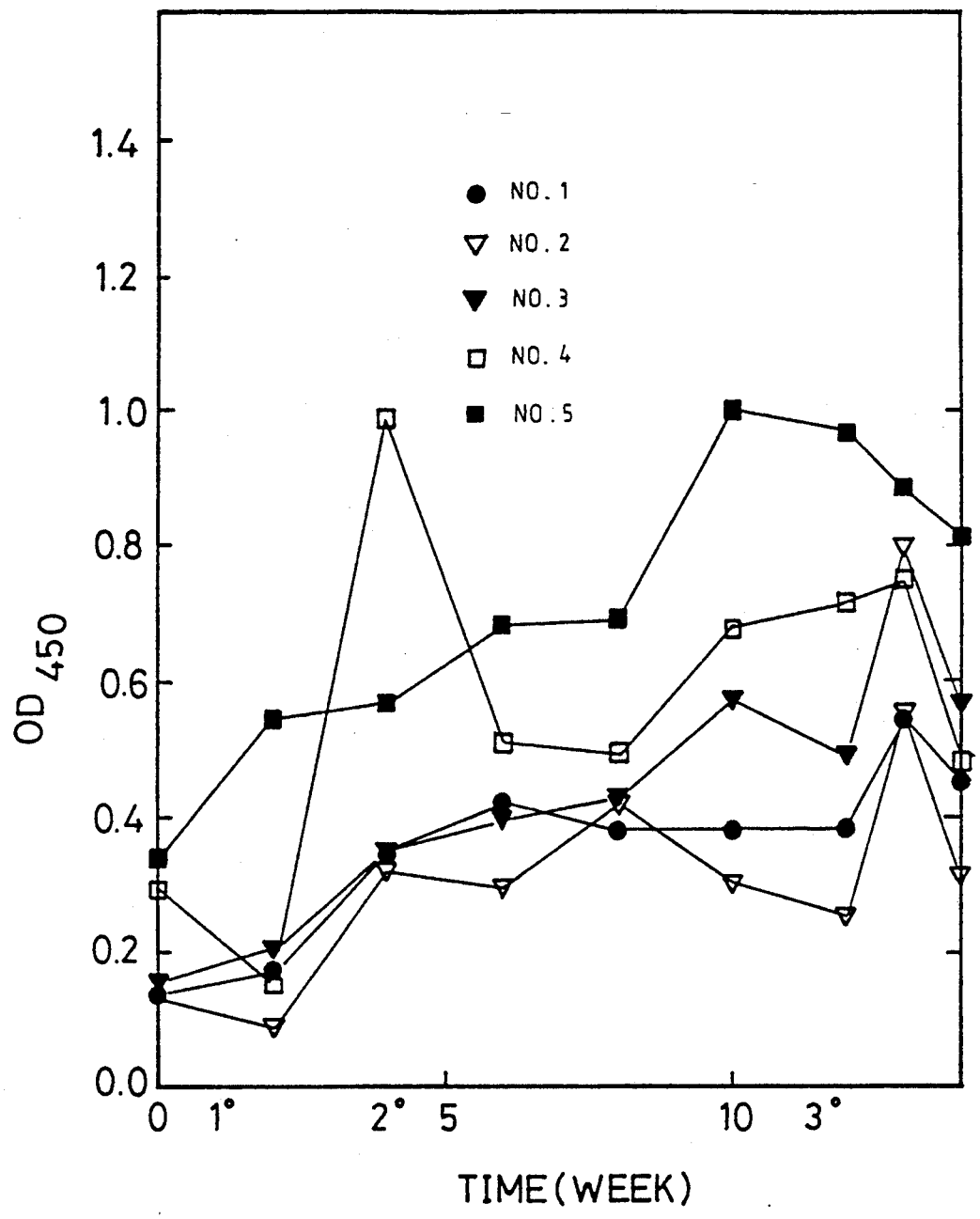

After 6 and 12 weeks, the original membrane was replaced with a new nitrocellulose membrane absorbed with the same dose of carbofuran. The animal's blood was sampled once a week before and after the immunization. Following diluting the serum samples to 400 fold in PBS, the serum thereof was tested by a carbofuran-ELISA which comprises adding the carbofuran, 5 μg/0.1 ml to a 96-well ELISA plate and drying, then blocking with 0.1% of skim milk; after 30 minutes, washing three times with PBST (0.05% Tween 20-PBS) and adding therein the serum to be tested (100 μg/well). Followed by reacting for 2 hours at 37° C., it was washed with PBST and reacted with biotin-rabbit-antimouse Ig and avidin-HRPO for 30 minutes, respectively, then washed again with PBST prior to adding thereto a substrate, tetramethylbenzidine solution and leaving to reaction for 20 minutes at room temperature in the dark. Finally, the reaction was stopped by 1N HCl. The results are shown in FIG. 4. It can be seen from FIG. 4 that, in comparison with the ELISA value of the serum before and after subcutaneous immunization, the immune response against a hapten (carbofuran) was simulated in all 5 mice. Two mice (No. 4 and 5); had the most potent immunity, with the immune response taking place after fist immunization. The other three (No. 1, 2 and 3) had the titer thereof increased with the increasing immunization frequency. In view of the above, the method of the present invention can also stimulate an immune response in vivo of the BALB/c mice.

From the above examples, it is shown that for the method of the invention, it is not necessary to form an analogue of a hapten first and then conjugate with a large molecular carrier as in the conventional technique, Therefore, the procedure and time are simplified and shortened.

In addition, in the process of the invention, since the structure of the hapten is maintained unchanged, the immune response produced exhibits specificity to the hapten only. Therefore, the screening step may be simplified.

What is claimed is:

1. A method of stimulating an immune response comprising:
   (a) preparing a solution of a hapten;
   (b) adhering said hapten to a solid support by contacting said hapten solution with said solid support;
   (c) drying said solid support to obtain a hapten-solid support complex; and
   (d) contacting in vivo or in vitro said hapten-solid support complex with lymphocytes; wherein said solid phase support is selected from the group consisting of hydrophilic cellulose mixed ester, nitrocellulose, cellulose acetate, nylon, polyvinylidone (PVDF), vinylbenzyl chloromethyl styrene, polyacrolein, hydrophobic polytetrafluoroethylene, polystyrene and silica gel.

2. The method as claimed in claim 1, wherein said solid phase support is a membrane, latex particles or microparticle beads.

3. The method as claimed in claim 2, wherein said solid phase support is a membrane.

4. The method as claimed in claim 1, wherein said drying is carried out by natural drying.

5. The method as claimed in claim 1, wherein said hapten is a carbofuran having a structural formula of:

$$\text{CH}_3\text{NHCOO}\text{-benzofuran-}O\text{-C(CH}_3)_2\text{-CH}_3$$

6. The method as claimed in claim 1, wherein said hapten is methamidophos.

7. The method as claimed in claim 1, wherein said solid phase support is a nitrocellulose membrane.

8. A method of preparing a hapten-solid phase support complex capable of stimulating an immune response, comprising:
   (a) preparing a solution of a hapten;
   (b) adhering said hapten to a solid phase support by contacting said hapten solution with said solid support; and
   (c) drying said solid support to obtain a hapten-solid support complex; wherein said solid phase support is selected from the group consisting of hydrophilic cellulose mixed ester, nitrocellulose, cellulose acetate, nylon, polyvinylidone (PVDF), vinylbenzyl chloromethyl styrene, polyacrolein, hydrophobic polytetrafluoroethylene, polystyrene and silica gel.

9. The method as claimed in claim 8, wherein said solid phase support is a membrane, latex particles or microparticle beads.

10. The method as claimed in claim 9, wherein said solid phase support is a membrane.

11. The method as claimed in claim 8, wherein said drying is carried out by natural drying.

12. The method as claimed in claim 9, wherein said hapten is carbofuran having a structural formula of:

$$\text{CH}_3\text{NHCOO}\text{-benzofuran-}O\text{-C(CH}_3)_2\text{-CH}_3$$

13. The method as claimed in claim 9, wherein said hapten is methamidophos.

14. The method as claimed in claim 9, wherein said solid phase support is a nitrocellulose membrane.

15. A hapten-solid phase support complex capable of stimulating an immune response, comprising:
   a hapten; and
   a solid phase support, wherein said hapten is adhered thereon; wherein said solid phase support is selected from the group consisting of hydrophilic cellulose mixed ester, nitrocellulose, cellulose acetate, nylon, polyvinylidone (PVDF), vinylbenzyl chloromethyl styrene, polyacrolein, hydrophobic polytetrafluoroethylene, polystyrene and silica gel.

16. The hapten-solid phase support complex as claimed in claim 15, wherein said solid phase support is a membrane, latex particles or microparticle beads.

17. The hapten-solid phase support complex as claimed in claim 16, wherein said solid phase support is a membrane.

18. The hapten-solid phase support complex as claimed in claim 15, wherein said hapten is a carbofuran having structural formula of:

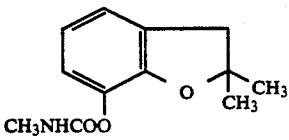

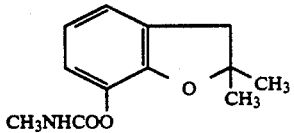

19. The hapten-solid phase support complex as claimed in claim 15, wherein said solid phase support is a methamidophos.

20. The hapten-solid phase support complex as claimed in claim 17, wherein said solid phase support is a nitrocellulose membrane.

* * * * *

19. The hapten-solid phase support complex as claimed in claim 15, wherein said solid phase support is a methamidophos.

20. The hapten-solid phase support complex as claimed in claim 17, wherein said solid phase support is a nitrocellulose membrane.

* * * * *